(12) United States Patent
Gatov

(10) Patent No.: US 6,412,358 B1
(45) Date of Patent: Jul. 2, 2002

(54) CLEANLINESS VERIFICATION SYSTEM

(75) Inventor: Michael S. Gatov, Troutdale, OR (US)

(73) Assignee: LSI Logic Corporation, Milpitas, CA (US)

( * ) Notice: Subject to any disclaimer, the term of this patent is extended or adjusted under 35 U.S.C. 154(b) by 81 days.

(21) Appl. No.: 09/639,449

(22) Filed: Aug. 15, 2000

(51) Int. Cl.⁷ .............................................. G01N 1/14
(52) U.S. Cl. ................................................. 73/864.71
(58) Field of Search ................. 73/28.01, 863.11, 73/863.12, 864.35, 864.71, 865.5; 340/627, 632; 901/46, 50; 356/440, 438

(56) References Cited

U.S. PATENT DOCUMENTS

| | | | |
|---|---|---|---|
| 3,362,141 A | * | 1/1968 | Royster, Jr. et al. ..... 73/864.33 |
| 5,859,375 A | * | 1/1999 | Danylewych-May et al. ............ 73/864.71 |
| 5,939,647 A | * | 8/1999 | Chinn et al. ............. 73/864.71 |
| 5,942,699 A | * | 8/1999 | Ornath et al. ............ 73/863.12 |
| 6,053,059 A | * | 4/2000 | Muranaka et al. ....... 73/863.12 |
| 6,065,354 A | * | 5/2000 | Dinsmore ................ 73/863.12 |
| 6,125,687 A | * | 10/2000 | McClelland et al. ..... 73/863.12 |

FOREIGN PATENT DOCUMENTS

EP 0339561 * 11/1989 .............. 73/864.33

* cited by examiner

*Primary Examiner*—Robert Raevis
(74) *Attorney, Agent, or Firm*—Luedeka, Neely & Graham

(57) ABSTRACT

A method for detecting contaminants on an implement. A stream of gas is directed over at least a portion of the implement, to entrain at least a portion of the contaminants on the implement, and produce a contaminant laden stream of gas. At least a portion of the contaminant laden stream of gas is sampled, and the amount of contaminants in the sampled portion of the contaminant laden stream of gas is measured. The amount of contaminants in the sampled portion of the contaminant laden stream of gas is reported.

17 Claims, 1 Drawing Sheet

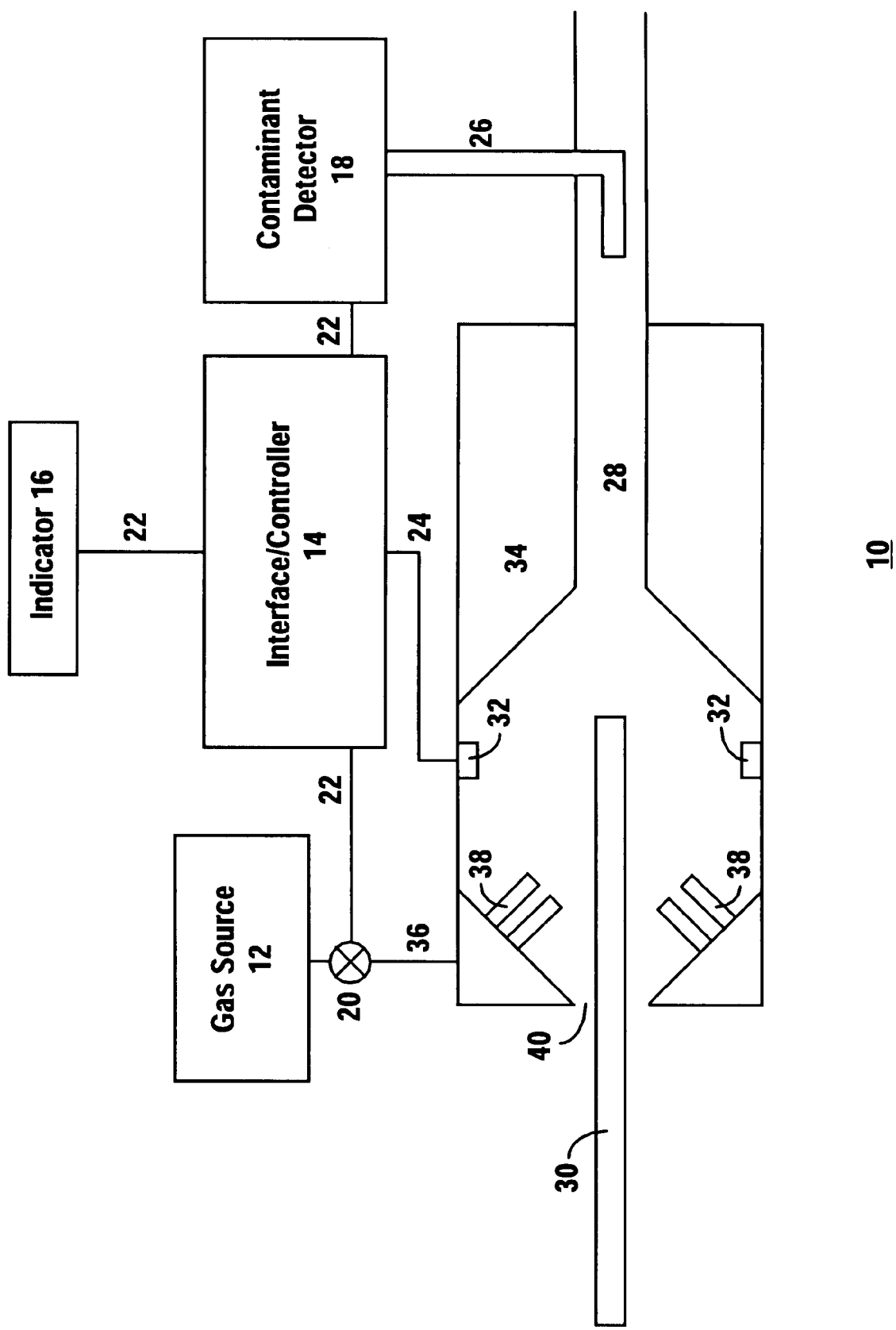

CLEANLINESS VERIFICATION SYSTEM

FIELD

This invention relates to the field of determining the level of cleanliness of semiconductor processing equipment components. More particularly the invention relates to determining the contamination level of an end effector.

BACKGROUND

Many types of semiconductor manufacturing equipment utilize robotic end-effectors to transport wafers between locations. Some processes have a high probability of cross-contaminating the wafers by means of the end-effectors. Metal deposition tools, and in particular, copper deposition tools are likely to cross-contaminate the backsides of the wafers. Because this contamination can take place at any time, it is necessary to frequently check the cleanliness condition of the wafer handling devices. Due to lost production time and realignment issues, it is preferable to measure the contaminant levels on the end-effectors without requiring any disassembly. What is needed, therefore, is a system for verifying the cleanliness of implements, such as end effectors, that does not physically contact the implement and does not require that the implement be removed from the equipment to which it is attached.

SUMMARY

The above and other needs are met by a method for detecting contaminants on an implement. A stream of gas is directed over at least a portion of the implement, to entrain at least a portion of the contaminants on the implement, and produce a contaminant laden stream of gas. At least a portion of the contaminant laden stream of gas is sampled, and the amount of contaminants in the sampled portion of the contaminant laden stream of gas is measured. The amount of contaminants in the sampled portion of the contaminant laden stream of gas is reported.

Because a stream of gas is used to entrain the contaminants on the implement, the implement is not physically contacted by something that could potentially damage it. Further, the stream of gas can be directed over the implement without removing the implement from the equipment to which it is attached.

In various preferred embodiments, the implement is inserted into a chamber, where the presence of the implement is detected, which triggers the stream of gas. The gas is preferably air, nitrogen, argon, or an inert gas. The stream of gas may be directed over the entire implement, and the implement may be rotated within the stream of gas while the stream of gas is directed over the implement.

In alternate embodiments the step of measuring the amount of contaminants can be accomplished either by counting particles in the sampled portion of the contaminant laden stream of gas with a particle counter, or by detecting the contaminants in the sampled portion of the contaminant laden stream of gas with a residual gas analyzer.

The amount of contaminants can be reported in a variety of different ways. For example, an indicator light is illuminated when the amount of contaminants in the sampled portion of the contaminant laden stream of gas is below a predetermined limit. Alternately, an indicator light is illuminated when the amount of contamination in the sampled portion of the contaminant laden stream of gas is above the predetermined limit, or two indicator lights can be provided, each with separate limits. Further, violation of the predetermined limit can trigger an audible alarm.

In a most preferred embodiment, when the amount of contaminants in the sampled portion of the contaminant laden stream of gas is above a predetermined limit, then continued use of the implement is prohibited without operator intervention. Conversely, when the amount of contaminants in the sampled portion of the contaminant laden stream of gas is below a predetermined limit, then continued use of the implement is permitted without operator intervention.

An apparatus according to the present invention has a gas discharge for directing a stream of gas over at least a portion of the implement, to entrain at least a portion of the contaminants on the implement, and thereby produce a contaminant laden stream of gas. A gas sampler samples at least a portion of the contaminant laden stream of gas, and a contaminant detector measures the amount of contaminants in the sampled portion of the contaminant laden stream of gas. An indicator reports the amount of contaminants in the sampled portion of the contaminant laden stream of gas.

BRIEF DESCRIPTION OF THE DRAWINGS

Further advantages of the invention are apparent by reference to the detailed description when considered in conjunction with the figure, which is not to scale so as to more clearly show the details, and which depicts a functional block diagram of an apparatus according to the present invention.

DETAILED DESCRIPTION

Referring now to the figure, there is depicted a functional block diagram of the apparatus 10 according to a preferred embodiment of the invention. The apparatus 10 is designed to detect the contamination that is present on the implement 30. Although some amount of cleaning of the implement 30 occurs during this process, as a small amount of contaminants are removed from the implement 30 as the stream of gas passes over it, the primary purpose of the apparatus 10 is not to clean the implement 30, but to provide a means by which it can be determined whether the implement 30 requires cleaning.

The implement 30 is inserted into the apparatus 10 through an insertion slot 40. In various embodiments the insertion slot 40 includes a means of some sort to make a seal of some degree to the surfaces of the implement 30, such as plastic bristles or flaps. However, in the preferred embodiment the insertion slot 40 is merely an opening in the enclosure 34 of the apparatus 10, which opening is only slightly larger than the implement 30 that the insertion slot 40 is designed to accept. The purpose of providing an opening that is only slightly larger than the implement 30, or providing sealing means as mentioned above, is to reduce the amount of extraneous contamination that may enter the apparatus 10 through the insertion slot 40 from sources other than the implement 30. Such extraneous contamination may tend to give false readings of contamination in regard to the implement 30 when it is tested, as described below.

In a most preferred embodiment the enclosure 34 and the insertion slot 40 are designed to receive as much of the implement 30 as practical. In this manner, a larger and perhaps more representative sampling of the contaminants on the implement 30 is made. In the limit, where the entire implement 30 is received within the enclosure 34, a complete sampling of the implement 30 is made. However, in other embodiments there are other methods that are employed to provide for a larger sampling of the implement 30. For example, if the implement 30 is rotatable, such as in the case of an end effector, then the implement 30 is placed into the enclosure 34 through the insertion slot 40 to a point on the implement 30 that is at or near the rotational hub, and the implement 30 is then rotated through the enclosure 34 so that substantially all of the implement 30 is sampled over a period of time.

The implement 30 is preferably inserted into the enclosure 34 through the insertion slot 40 until it is detected by an implement detector 32. The implement detector 32 may take the form of one or more different detection devices, such as a radiation beam that is broken when the implement 30 is inserted to a sufficient degree within the enclosure 34. The implement detector 32 provides several important functions in the course of the operation of the apparatus 10. For example, as alluded to above, the implement detector 32 indicates when the implement 30 is sufficiently inserted and the cleanliness verification can commence. Further, the implement detector 32 preferably triggers other elements of the apparatus 10, as more fully described below, so that the operation of the apparatus 10 is more automated and requires little or no operator involvement.

After the implement 30 is inserted into the enclosure 34 to a desired degree and rotation of the implement 30, if desired, has commenced, a stream of gas is passed over the surfaces of the implement 30. In a most preferred embodiment, the stream of gas is provided by a gas discharge system that includes a gas source 12, a valve 20, and ports 38. A gas delivery line 36 delivers the gas from the gas source 12 to the ports 38. The gas discharge system directs the stream of gas over at least a portion of the implement 30. The valve 20 operates to open the gas source 12 to the ports 38 when the gas stream is desired, and then close the gas source 12 to the ports 38 when the gas stream is not desired. The ports 38 form the gas supplied by the gas source 12 into a stream of gas, and direct the stream of gas over the implement 30.

The gas source 12, from which the stream of gas is formed, preferably comprises a gas that will not confound the results of the cleanliness verification process performed by the apparatus 10. For this reason, the gas is preferably a relatively non reactive gas, such as nitrogen, air, argon, or some inert gas. Further, the gas source 12 preferable provides a gas that is clean, in that it does not contain unwanted vapors or particles that tend to skew the results of the analysis. Additionally, the gas is preferably dry, at least to a moderate degree, so that any moisture within the gas does not cause particulate matter to adhere more tightly to the implement 30 being tested, or clump smaller particles into larger aggregate, or react with whatever chemical contaminants may be present on the implement 30. A source of clean, dry nitrogen is preferred for use in most situations, and also tends to be less expensive than acceptable choices.

The valve 20 is preferably connected to a communication means 22, such as an electrical signal on a wire or a mechanical linkage, which is in turn connected to an interface or controller 14. The controller 14 is similarly in communication with some of the other elements of the apparatus 10, such as the implement detector 32 via communication means 24, which is preferable an electrical connection. By use of the communication means 24, the controller 14 is made aware of when the implement detector 32 detects the proper insertion of the implement 30. The controller 14 then signals the valve 20 via communication means 22 to open, which permits the gas from the gas source 12 to flow through the gas supply line 36 to the ports 38, where it is formed into a gas stream. Thus, the controller 14, acting in cooperation with the other elements of the apparatus 10 as described above, provides a degree of automation to the apparatus 10.

As the stream of gas passes over the surface of the implement 30, it tends to entrain whatever manner of contamination may happen to reside on the surface of the implement 30. For example, if there are particles on the surface of the implement 30, then the gas stream tends to entrain the particles. Further, if there is some manner of chemical contamination on the surface of the implement 30, then the chemical contamination also tends to be entrained within the stream of gas to some degree as it flows over the surface of the implement 30. As the gas stream flows over the surface of the implement 30 and the contamination from the surface of the implement 30 is entrained in the gas stream, a contaminant laden stream of gas is produced.

So that the results of the cleanliness verification process are more readily compared from time to time between different tests, the delivery of the gas stream through the ports 38 is preferably maintained at a desired orientation in relation to the implement 30. This desired orientation is preferably maintained by the enclosure 34, to which the ports 38 are preferably mounted, and which receives the implement 30 at a desired orientation, which is maintained by the specific configuration of the insertion slot 40. The enclosure 34 is preferably formed of stainless steel or some other durable and resilient material, so that the structural integrity of the enclosure 34 is reliably maintained over time, and also so that contaminants are less likely to slough off from or be absorbed by the walls of the enclosure 34, which would tend to obscure the results of the cleanliness verification process conducted within the apparatus 10.

The contaminant laden stream of gas is directed down an exhaust port 28 towards a gas sampler 26. The flow of the contaminant laden stream of gas is preferably between about 1.0 scfm and about 3.0 scfm, and most preferably about 1.0 scfm. The flow of the contaminant laden stream of gas is, in one embodiment, provided entirely under the force provided by the gas as it is ejected through the ports 38. Alternately, the flow of the contaminant laden stream of gas is drawn by an exhaust source, such as a fan, that is connected to the exhaust port 28 at the opposite end of the exhaust port 28 from the enclosure 34. In this latter configuration, the contaminant laden stream of gas may comprise gas from the gas source 12 that is discharged through the ports 38, and ambient gasses that are drawn into the enclosure 34 through the insertion slot 40 and elsewhere.

The gas sampler 26 samples at least a portion of the contaminant laden stream of gas. Preferably, the gas sampler 26 samples between about 0.1 scfm and about 1.0 scfm, and most preferably about 0.1 scfm of the contaminant laden stream of gas. In some embodiments this represent only a fraction of the total flow of the contaminant laden stream of gas, and in alternate embodiments this represents all of the flow of the contaminant laden stream of gas.

The portion of the contaminant laden stream of gas that is sampled by the gas sampler 26 is directed to the contaminant detector 18, which detects and measures the amount of contaminants in the sampled portion of the contaminant laden stream of gas. The contaminant detector 18 is preferably connected to the controller 14 via communication means 22. In this manner, the contamination detector 18 is signaled by the controller 14 to commence operation at a point in time as determined by the controller 14. For example, upon insertion of the implement 30 and commencement of the flow of gas from the ports 38, as described above, the controller 14 signals the contaminant detector 18 to enable the gas sampler 26 and start detecting contaminants within the contaminant laden stream of gas. Alternately, the controller 14 instructs the contaminant detector 18 to wait for some predetermined length of time after the commencement of the gas flow before sampling and measuring the contaminant laden stream of gas. Thus, the controller 14 also preferably provides this additional degree of automation for the apparatus 10.

The contaminant detector 18 may take one or more of several different forms of contamination detectors. In the most preferred embodiment, where the implement 30 being tested is an end effector, the contaminant detector is preferably a particle detector, such as is used to detect, measure, and count airborne particles entrained within a stream of gas. In this embodiment, the contaminant detector 18 may have the full capabilities to sense and bin the particulate contamination within the sampled contaminant laden stream of gas as to size, and then provide counts of the particles within the various bins. However, in a more basic embodiment, the contaminant detector 18 only has the ability to sense and count particles, but the ability to bin the particles by size and provide counts for the individual bins is not required nor provided.

In an alternate embodiment in which contaminants of a type other than particulate matter is to be detected, such as chemical contamination, the contaminant detector 18 is a sensor of a different type that is specifically selected so as to have the capability to detect the contamination type that is to be sensed. For example, a residual gas analyzer is used in various embodiments to detect residual gaseous contaminants, such as may be entrained from chemical contamination on the surface of the implement 30 by the stream of gas. In yet a further embodiment, the contaminant detector 18 is a plurality of one or more different types of contaminant detectors, such as particle counters and residual gas analyzers, which are connected to the gas sampler 26 in either a parallel or a serial manner, or a combination of the two.

The information in regard to the degree of contamination present within the contaminant laden stream of gas is preferably provided to the controller 14 by the contaminant detector 18 via the communication means 22. In one embodiment, the controller 14 makes an analysis, such as one based on empirical data, to correlate the amount of contaminants in the sampled portion of the contaminant laden stream of gas to a level of the contaminants on the implement 30. The controller 14 preferably provides a report of the results of the cleanliness verification process to the indicator 16 via communication means 22. The indicator 16 may take any one or more of a variety of different forms, as described in more detail below.

For example, the indicator 16 may be as simple as one or more indicator lights. One light, for example a green light, illuminates when the contamination is below a predetermined limit, and another light, for example a red light, illuminates when the contamination is above the predetermined limit. In alternate embodiments, only a single light is used. For example, when the limit is not violated a green light is illuminated, but when the limit is violated, the green light is not illuminated. Conversely, in another embodiment, a red light is illuminated when the limit is violated, but when the limit is not violated, the red light is not illuminated. In yet further embodiments, sound is used as the indicator 16, either alone or in combination with the other methods as described herein. For example, if the predetermined limit is violated, then an alarm sounds, but when the predetermined limits is not violated, then no alarm sounds. Of course, there are also various permutations of using sound as the indicator 16, which are generally analogous to the examples of using light as the indicator 16, described above.

In a more elaborate embodiment, where the implement 30 is an end effector mounted to a piece of processing equipment, the processing equipment is programmed to bring the end effector to the apparatus 10 for testing at regularly determined intervals. The robotic arm to which the end effector is mounted inserts the end effector into the enclosure 34 through the insertion slot 40, and the apparatus 10 automatically initiates the stream of gas and takes readings as described above. In embodiments such as this, the indicator 16 may take the form of an interlock, such as an electrical interlock, that is wired to the processing equipment, or to a computer that is in communication with or controls the operation of the processing equipment.

In this embodiment the interlock functions to prohibit continued use of the implement 30 when the amount of contaminants in the sampled portion of the contaminant laden stream of gas is above the predetermined limit, unless an operator overrides the interlock. Further, the interlock functions to permit automated and continued use of the implement 30 when the amount of contaminants in the sampled portion of the contaminant laden stream of gas is below the predetermined limit. In this manner, the entire process of verifying the cleanliness of the end effector is made completely automatic and requires no operator intervention unless the apparatus 10 signals a need for the end effector to be removed and cleaned.

In one embodiment, all of the elements of the apparatus 10 as described above are contained within the enclosure 34, although preferably not all of the elements are within a portion of the enclosure 34 where they contact the stream of gas or the contaminant laden stream of gas. However, in alternate embodiments the various elements are separated one from another, within the constraints as described above, so that the enclosure 34 can be commensurately smaller and less obtrusive when mounting, such as to or near a piece of processing equipment. The other elements of the apparatus 10 in this embodiment are then connected to the enclosure 34 via wires, tubes, or linkage as appropriate for the individual connection in question.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as is suited to the particular use contemplated. All such modifications and variations are within the scope of the invention as determined by the appended claims when interpreted in accordance with the breadth to which they are fairly, legally, and equitably entitled.

What is claimed is:

1. A method for detecting contaminants on an implement, comprising the steps of:
    directing a stream of gas over at least a portion of the implement to entrain at least a portion of the contaminants on the implement and produce a contaminant laden stream of gas,
    rotating the implement within the stream of gas concurrently with the step of directing the stream of gas over the implement,
    sampling at least a portion of the contaminant laden stream of gas, measuring an amount of contaminants in the sampled portion of the contaminant laden stream of gas, and reporting the amount of contaminants in the sampled portion of the contaminant laden stream of gas.

2. The method of claim 1 further comprising the following preliminary steps:

inserting the implement into a chamber, detecting the implement inside of the chamber, and triggering the stream of gas when the implement is detected inside of the chamber.

3. The method of claim 1 wherein the stream of gas further comprises at least one of air, nitrogen, argon, and an inert gas.

4. The method of claim 1 wherein the step of directing the stream of gas further comprises directing a stream of gas over the entire implement.

5. The method of claim 1 wherein the step of sampling at least a portion of the contaminant laden stream of gas further comprises collecting substantially all of the contaminant laden stream of gas for analysis.

6. The method of claim 1 wherein the step of measuring the amount of contaminants further comprises counting particles in the sampled portion of the contaminant laden stream of gas with a particle counter.

7. The method of claim 1 wherein the step of measuring the amount of contaminants further comprises detecting the contaminants in the sampled portion of the contaminant laden stream of gas with a residual gas analyzer.

8. The method of claim 1 wherein the step of reporting the amount of contaminants further comprises triggering an alarm when the amount of contaminants in the sampled portion of the contaminant laden stream of gas exceeds a predetermined limit.

9. The method of claim 1 wherein the step of reporting the amount of contaminants further comprises illuminating an indicator light when the amount of contaminants in the sampled portion of the contaminant laden stream of gas is below a predetermined limit.

10. The method of claim 1 wherein the step of reporting the amount of contaminants further comprises:

prohibiting continued use of the implement without operator intervention when the amount of contaminants in the sampled portion of the contaminant laden stream of gas is above a predetermined limit, and permitting continued use of the implement without operator intervention when the amount of contaminants in the sampled portion of the contaminant laden stream of gas is below a predetermined limit.

11. The method of claim 1 further comprising the subsequent step of correlating the amount of contaminants in the sampled portion of the contaminant laden stream of gas to a level of the contaminants on the implement.

12. An apparatus for detecting contaminants on an implement, comprising:

a gas discharge for directing a stream of gas over at least a portion of the implement to entrain at least a portion of the contaminants on the implement and produce a contaminant laden stream of gas, an enclosure for maintaining a desired orientation between the gas discharge and the implement, the enclosure having, an insertion slot through which the implement is inserted into the enclosure, and an exhaust port through which the contaminant laden stream of gas exits the enclosure, a gas sampler for sampling at least a portion of the contaminant laden stream of gas, a contaminant detector for measuring an amount of contaminants in the sampled portion of the contaminant laden stream of gas, an indicator for reporting the amount of contaminants in the sampled portion of the contaminant laden stream of gas, an implement detector for detecting the implement inside the enclosure, and an interface for signaling at least one of the gas discharge and the contaminant detector when the implement detector detects the implement inside the enclosure.

13. The apparatus of claim 12 wherein the gas discharge, the gas sampler, the contaminant detector, and the indicator are disposed within the enclosure.

14. The apparatus of claim 12 wherein the gas discharge further comprises:

a gas source for providing a gas, ports for directing the gas over the implement as the stream of gas, and a valve for opening the gas source to and closing the gas source from the ports.

15. The apparatus of claim 12 wherein the contaminant detector further comprises a particle counter for sensing particles in the sampled portion of the contaminant laden stream of gas.

16. The apparatus of claim 12 wherein the indicator further comprises:

an interlock for prohibiting continued use of the implement without operator intervention when the amount of contaminants in the sampled portion of the contaminant laden stream of gas is above a predetermined limit, and the interlock further for permitting continued use of the implement without operator intervention when the amount of contaminants in the sampled portion of the contaminant laden stream of gas is below a predetermined limit.

17. An apparatus for detecting particles on an end effector, comprising:

a gas discharge for directing a stream of gas over at least a portion of the end effector to entrain at least a portion of the particles on the end effector and produce a particle laden stream of gas, the gas discharge having, a gas source for providing a gas, ports for directing the gas over the end effector as the stream of gas, and a valve for opening the gas source to and closing the gas source from the ports, an enclosure for maintaining a desired orientation between the gas discharge and the end effector, the enclosure forming an insertion slot through which the end effector is inserted into the enclosure, an end effector detector for detecting the end effector inside the enclosure, an interface for signaling at least one of the gas discharge and a particle counter when the end effector detector detects the end effector inside the enclosure, a gas sampler for sampling at least a portion of the particle laden stream of gas, the particle counter for sensing a number of particles in the sampled portion of the particle laden stream of gas, and an indicator for reporting the number of particles in the sampled portion of the particle laden stream of gas, the indicator having an interlock for prohibiting continued use of the end effector without operator intervention when the amount of particles in the sampled portion of the particle laden stream of gas is above a predetermined limit, and the interlock further for permitting continued use of the end effector without operator intervention when the amount of particles in the sampled portion of the particle laden stream of gas is below a predetermined limit.

* * * * *